(12) United States Patent
Schuele

(10) Patent No.: US 10,285,732 B2
(45) Date of Patent: May 14, 2019

(54) SKULL CLAMP

(71) Applicant: pro med instruments GmbH, Freiburg im Breisgau (DE)

(72) Inventor: Matthias E. Schuele, Freiburg (DE)

(73) Assignee: pro med instruments GmbH, Freiburg Im Breisgau (DE)

( * ) Notice: Subject to any disclaimer, the term of this patent is extended or adjusted under 35 U.S.C. 154(b) by 0 days.

(21) Appl. No.: 14/713,177

(22) Filed: May 15, 2015

(65) Prior Publication Data
US 2015/0327937 A1    Nov. 19, 2015

Related U.S. Application Data

(60) Provisional application No. 61/994,708, filed on May 16, 2014.

(51) Int. Cl.
| A61B 17/60 | (2006.01) |
| A61B 90/16 | (2016.01) |
| A61B 90/14 | (2016.01) |
| A61B 90/10 | (2016.01) |

(52) U.S. Cl.
CPC .............. *A61B 17/60* (2013.01); *A61B 90/14* (2016.02); *A61B 90/16* (2016.02); *A61B 2090/101* (2016.02)

(58) Field of Classification Search
CPC ..... A61B 17/6433; A61B 90/14; A61B 90/10; A61B 17/62; A61B 17/645
See application file for complete search history.

(56) References Cited

U.S. PATENT DOCUMENTS

| 2,966,383 | A | * | 12/1960 | Boetcker | A61B 90/14 378/180 |
| 5,269,034 | A | * | 12/1993 | Day | A61B 90/14 403/59 |
| 5,537,704 | A | * | 7/1996 | Dinkler | A61B 90/14 5/622 |
| D456,510 | S | | 4/2002 | Spetzler et al. | |
| 8,002,772 | B2 | | 8/2011 | Sarin et al. | |
| 8,221,435 | B2 | | 7/2012 | Arndt et al. | |
| 8,801,711 | B2 | | 8/2014 | Solomon et al. | |

(Continued)

FOREIGN PATENT DOCUMENTS

| DE | 10 2012 009584 | 11/2013 | |
| EP | 1488750 A1 * | 12/2004 | ......... A61B 17/6433 |
| WO | WO 2013/165095 | 11/2013 | |

OTHER PUBLICATIONS

International Search Report and Written Opinion dated Sep. 4, 2015 for Application No. PCT/IB2015/001082.

(Continued)

*Primary Examiner* — Julianna N Harvey
(74) *Attorney, Agent, or Firm* — Frost Brown Todd LLC

(57) ABSTRACT

A skull clamp for patient stabilization comprises a pair of arms where the arms include upright portions and lateral portions. The upright portions and lateral portions define longitudinal axes, where the intersection of these axes defines an arm angle that is greater than about 90 degrees. In some instances the arm angle is between about 100 and about 120 degrees. In some instances the arm angle is about 110 degrees. The skull clamp can have rails integrated in the arms for attaching various accessories to the skull clamp.

7 Claims, 11 Drawing Sheets

(56) References Cited

U.S. PATENT DOCUMENTS

| | | | | |
|---|---|---|---|---|
| 2001/0052151 A1* | 12/2001 | Reinhardt | ............... | A61B 90/14 5/637 |
| 2004/0102792 A1* | 5/2004 | Sarin | ....................... | A61B 34/20 606/151 |
| 2011/0226260 A1* | 9/2011 | Eder | ..................... | A61B 5/0555 128/845 |
| 2013/0081636 A1* | 4/2013 | Schuele | ................. | A61B 90/57 128/845 |
| 2014/0135765 A1 | 5/2014 | Schuele et al. | | |

OTHER PUBLICATIONS

Integra, MAYFIELD 2000 Skull Camp, accessed from http://www.integralife.com/index.aspx?redir=detailproduct&Product=160&ProductName=MAYFIELD%AE%202000%20Skull%20Clamp&ProductLineName=MAYFIELD%AE%20Standard%20Skull%20Clamps%20and%20Headrests&ProductLineID=63&PA=neurosurgeon, on Aug. 14, 2015. Publication date unknown at this time, please treat as prior art until proven otherwise.

Integra, MAYFIELD Infinity Skull Clamp, accessed from http://www.integralife.com/index.aspx?redir=detailproduct&Product=253&ProductName=MAYFIELD%AE%20Infinity%20Skull%20amp&ProductLineName=MAYFIELD%AE%20Standard%20Skull%20Clamps%20and%20Headrests&ProductLineID=63&PA=neurosurgeon, on Aug. 14, 2015. Publication date unknown at this time, please treat as prior art until proven otherwise.

Integra, MAYFIELD Modified Skull Clamp, accessed from http://www.integralife.com/index.aspx?redir=detailproduct&Product=159&ProductName=MAYFIELD%AE%20Modified%20Skull%20Clamp&ProductLineName=MAYFIELD%AE%20Standard%20Skull%20Clamps%20and%20Headrests&ProductLineID=63&PA=neurosurgeon, on Aug. 14, 2015. Publication date unknown at this time, please treat as prior art until proven otherwise.

Integra, MAYFIELD Triad Skull Clamp, accessed from http://www.integralife.com/index.aspx?redir=detailproduct&Product=158&ProductName=MAYFIELD%AE%20Triad%99%20Skull%20Clamp&ProductLineName=MAYFIELD%AE%20Standard%20Skull%20Clamps%20and%20Headrests&ProductLineID=63&PA=neurosurgeon, on Aug. 14, 2014. Publication date unknown at this time, please treat as prior art until proven otherwise.

Pro med instruments, "DORO® Skull Clamp Aluminum—Neurosurgical Head Holder," Item No. 1003-00, Feb. 12, 2015, downloaded from http://www.integralife.com/index.aspx=redir=detailproduct&Poduct=343&ProductName=MAYFIELD%AE%20Infinity%20XR2%20Radiolucent%20Skull%20Clamp&ProductLineName=MAYFIELD%AE%20Radiolucent%20Skull%20Clamps%20and%20Headrests&ProductLineID=65&PA=Neurosurgeon, 1 pg.

Integra, "MAYFIELD® Infinity XR2 Radiolucent Skull Clamp," 2010, downloaded from http://www.integralife.com/index.aspx?redir=detailproduct&Product=343&PoductNameMAYFIELD%AE%20Infinity%20XR2%20Radiolucent%20Skull%20Clamp&ProductLineName=MAYFIELD%AE%20Radiolucent%20Skull%20Clamps%20and%20Headrests&ProductLineID=65&PA=Neurosurgeon, 2 pgs.

\* cited by examiner

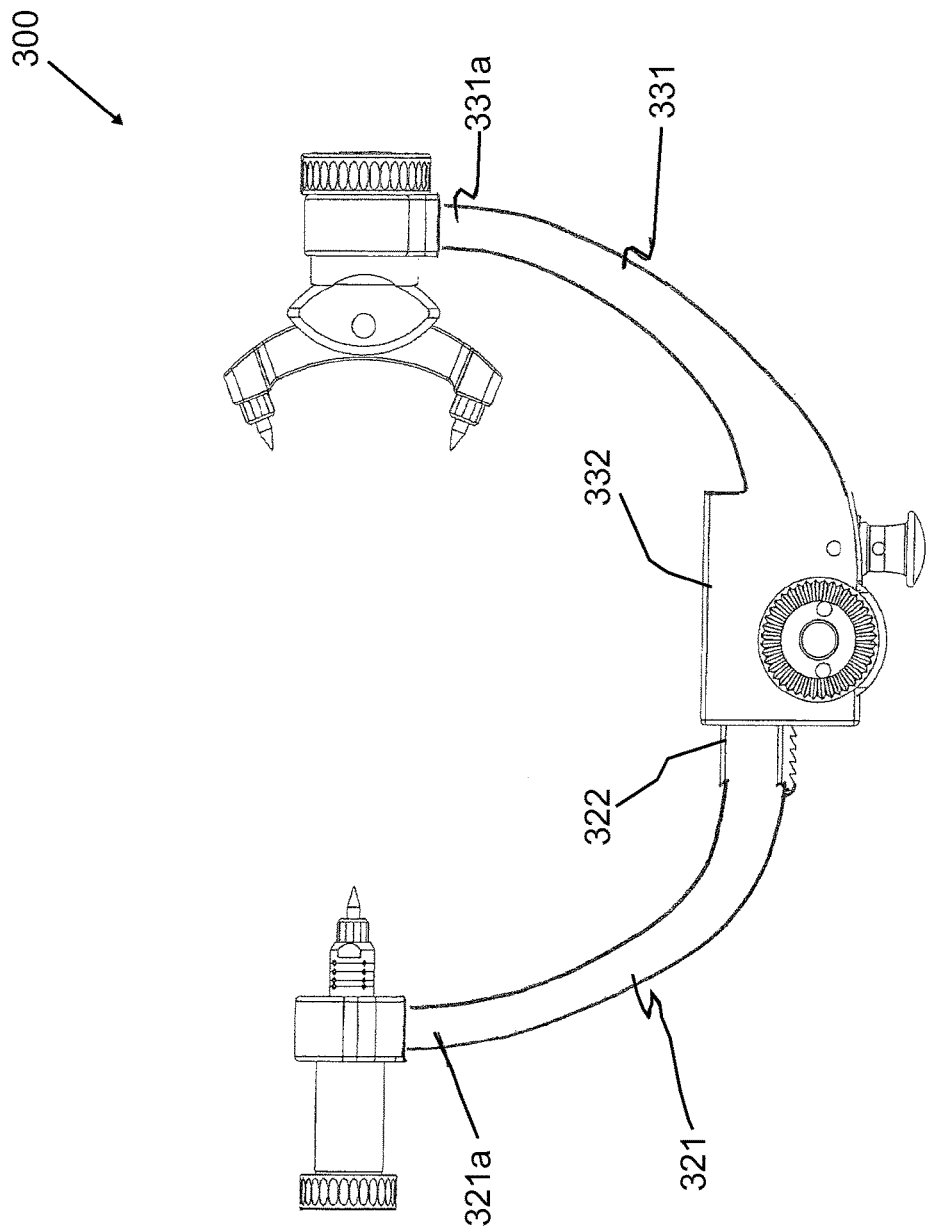

SKULL CLAMP

PRIORITY

This application claims priority to U.S. Provisional Patent Application Ser. No. 61/994,708, filed May 16, 2014, entitled "Skull Clamp," the disclosure of which is incorporated by reference herein.

BACKGROUND

During surgical operations or other procedures, a portion of the body upon which surgery is being conducted may be substantially immobilized, such as, for example, a patient's head during head or neck surgery. Such immobilization of a patient's head, for example, may be accomplished with a fixture such as head fixation device in the form of a skull clamp, halo, or other form. It may be desirable to have one or more surgical accessories or additional fixtures securely attached or mounted close at hand during the procedure. In some circumstances, it may be desirable and convenient to have such accessories or fixtures mounted directly to the fixture used for immobilization. In addition, it may be desirable to permit the selective attachment and/or adjustment of such accessories or fixtures. Of course, such features are not required. Also, it may be desirable and convenient that the fixture is compatible with certain imaging techniques and devices both in terms of modality and imaging equipment configurations, e.g. gantry size, etc.

While a variety of fixtures and accessories for attaching to fixtures have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain embodiments taken in conjunction with the accompanying drawings, in which like reference numerals identify the same elements.

FIG. 11 depicts another example skull clamp.

Figure 1:
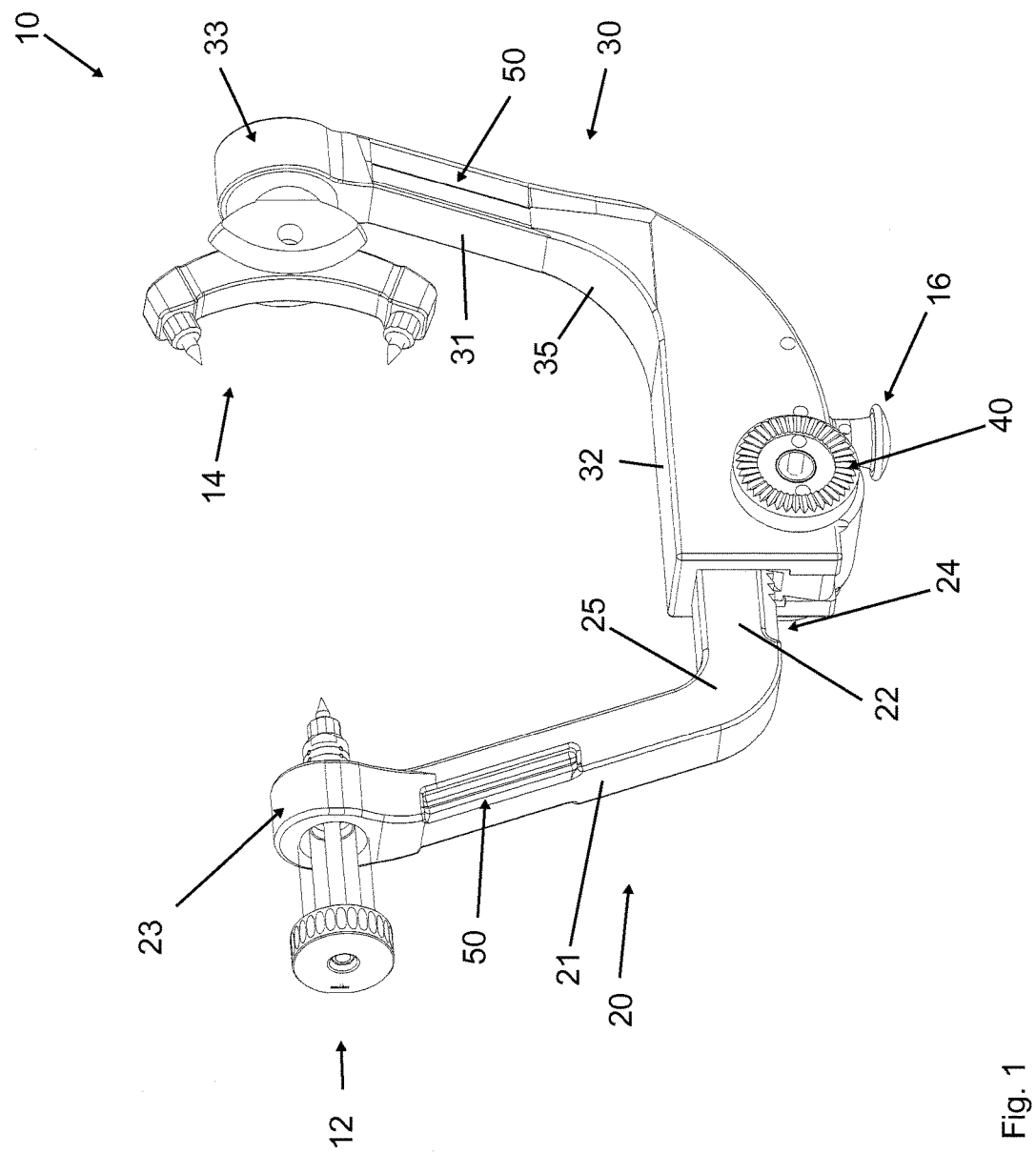
FIG. 1 depicts a perspective view of an example skull clamp.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain embodiments of the present disclosure should not be used to limit the scope of the present disclosure. Other examples, features, aspects, embodiments, and advantages of the invention will become apparent to those skilled in the art from the following description. As will be realized, various aspects of the present disclosure may take alternate forms, or have alternate or additional embodiments, without departing from the scope of the present disclosure. Accordingly, the drawings and descriptions should be regarded as illustrative in nature and not restrictive.

FIGS. 1-11 depict examples of a fixture, more specifically various head fixation devices in the form of skull clamps (10, 100, 200, 300). The difference between skull clamp (10) and skull clamp (100) is that skull clamp (10) includes attachment regions or rails (50) as described further below. With the exception of the attachment regions or rails (50) feature, the description of skull clamp (10) applies equally to skull clamp (100). Therefore skull clamp (100) is not described separately, it being understood that the description of skull clamp (10) fully describes skull clamp (100). The differences between skull clamp (10) and skull clamps (200, 300) will be explained in further detail below.

FIGS. 1-8 depict skull clamp (10) comprising a first arm (20) and a second arm (30). First arm (20) comprises an upright portion (21), a lateral portion (22), and an end or bore (23). Upright portion (21) comprises a first end (21a) and a second end (21b). First end (21a) connects with end (23), which is configured to receive a first pin assembly (12). First pin assembly (12) is configured to contact a patient's head during stabilization or immobilization. Second end (21b) of upright portion (21) connects with lateral portion (22). In some instances the connection between second end (21b) and lateral portion (22) is direct while in other instances it can be indirect. For instance, the connection may be indirect where curved portion (25) is between upright portion (21) and lateral portion (22). Lateral portion (22) comprises a first end (22a), a second end (22b), and an adjustable locking feature in the form of a toothed section (24). Toothed section (24) is received within second arm (30) as described below.

Second arm (30) comprises an upright portion (31), a lateral portion (32), and an end or bore (33). Upright portion (31) comprises a first end (31a) and a second end (31b). First end (31a) connects with end (33), which is configured to receive a second pin assembly (14). Second pin assembly (14) is configured to contact a patient's head during stabilization or immobilization. Second end (31b) of upright portion (31) connects with lateral portion (32). In some instances the connection between second end (31b) and lateral portion (32) is direct while in other instances it can be indirect. For instance, the connection may be indirect where curved portion (35) is between upright portion (31) and lateral portion (32). Lateral portion (32) comprises a first end (32a), a second end (32b), and an adjustable locking feature in the form of a slot (34). Slot (34) is configured to receive at least a portion of lateral portion (22) of first arm (20) having at least a portion of toothed section (24).

A locking pin (16) is configured with an engaging end that is positioned within slot (34) of second arm (30). The engaging end of locking pin (16) is configured to selectively engage or mate with toothed section (24) of first arm (20). Locking pin (16) is resiliently biased such that the engaging end of locking pin (16) is disposed in an engaging position relative to toothed section (24) when undisturbed.

To adjust skull clamp (10), first arm (20) and second arm (30) can be moved relative to one another, thereby adjusting the width of skull clamp (10) to accommodate patients of various size. To make such an adjustment, locking pin (16) is moved downward away from lateral portion (32) of second arm (30). This pulls the engaging end of locking pin (16) downward and away from toothed section (24) of first arm (20) thereby disengaging the teeth. First arm (20) and second arm (30) can now be adjusted widthwise to change the spacing between first and second pin assemblies (12, 14).

In some other versions, skull clamp (10) can be modified such that locking pin (16) is repositioned from the bottom of skull clamp (10) to a side of skull clamp (10). In some such instances all or certain components and features can be replaced by other selectively locking features. One such example having a side clamp opening system is disclosed in U.S. Patent Application 2014/0135765, published May 15, 2014, entitled "Skull Clamp Opening Apparatus and Method," the disclosure of which is incorporated by reference herein.

Skull clamp (10) comprises starburst interfaces (40, 42), with one of starburst interfaces (40) located on a front surface of second arm (30) and one of starburst interfaces (42) located on a back surface of second arm (30). Starburst interfaces (40, 42) are configured to connect skull clamp (10) with other structures. For instance, either of starburst interfaces (40, 42) can be used to connect skull clamp (10) with an operating table. Such a connection may be made directly or indirectly through other structures such as a table adapter or other positioning unit or device. In view of the teachings herein, ways in which to use starburst interfaces (40, 42) to connect skull clamp (10) with other structures will be apparent to those of ordinary skill in the art.

Skull clamp (10) also comprises attachment regions or rails (50) along each of upright portions (21, 31) of first and second arms (20, 30) respectively. Rails (50) are formed within part of upright portions (21, 31), although in some other examples rails (50) could be separate structures attached to upright portions (21, 31). In the present example rails (50) define a dovetail-shaped outermost portion of upright portion (21, 31) and a void space. In other examples rails (50) can have a T-shape or I-beam shape. These shapes are generally understood to be the shapes formed from cross-sectional views taken transversely across attachment regions or rails (50). With such rails (50) of skull clamp (10) various clamping accessories can be selectively attached with skull clamp (10). By way of example only, and not limitation, an example accessory for attachment to rail (50) may be a retractor arm, instrument positioning device, surgical armrest, etc. In view of the teachings herein, various ways to configure rails (50) and various accessories for use with rails (50) will be apparent to those of ordinary skill in the art. Furthermore, rails (50) are not required in all versions.

Skull clamp (10) is configured such that arms (20, 30) are angled, with upright portions (21, 31) oriented at an angle relative to lateral portions (22, 32) respectively where the angle formed is not perpendicular. In other words, upright portion (21) is not perpendicular with lateral portion (22), and likewise upright portion (31) is not perpendicular with lateral portion (32). Instead, upright portions (21, 31) and respective lateral portions (22, 32) form an angle at or about where they meet that is greater than about 90 degrees.

Figure 2:
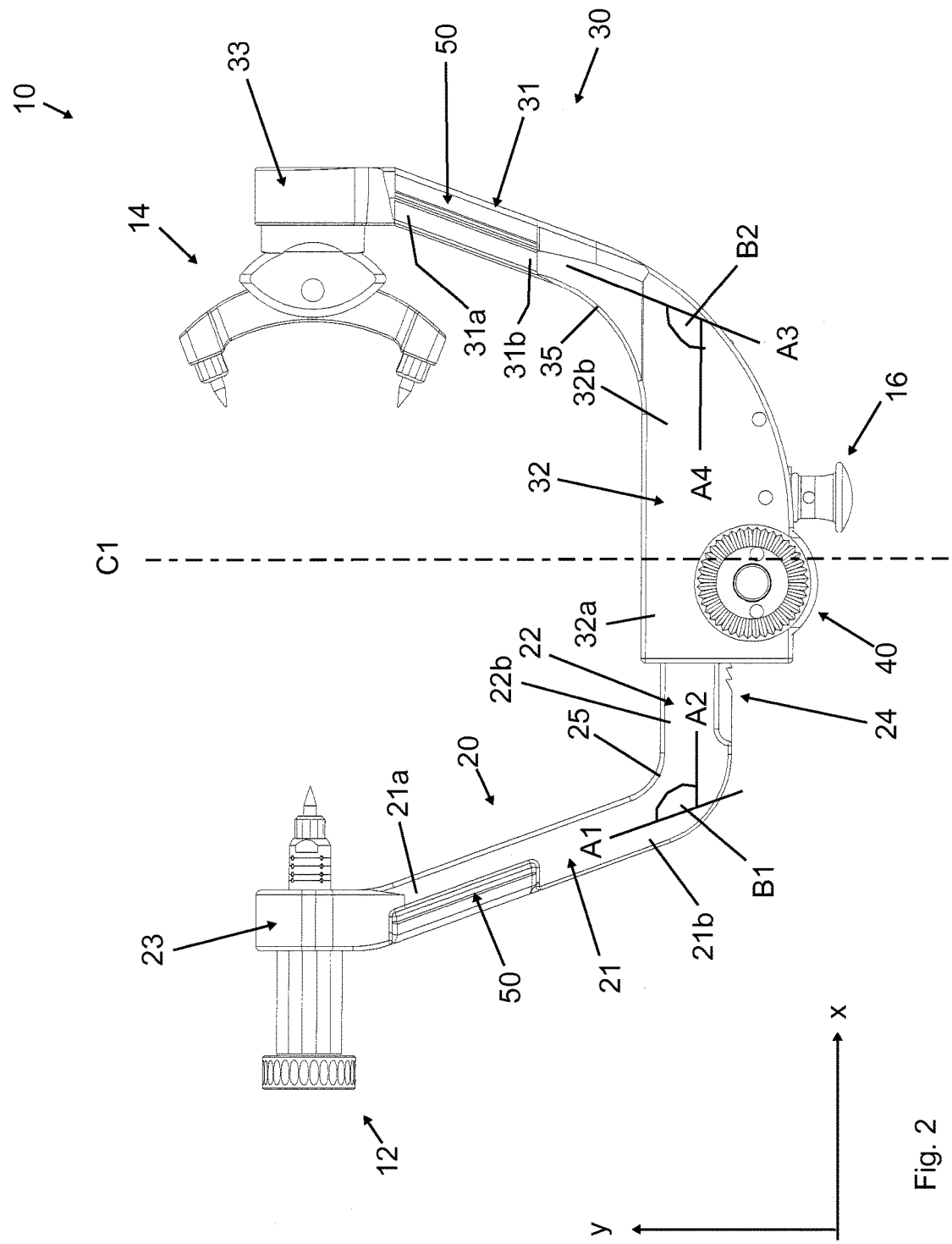
FIG. 2 depicts a front view of the skull clamp of FIG. 1.
Figure 3:
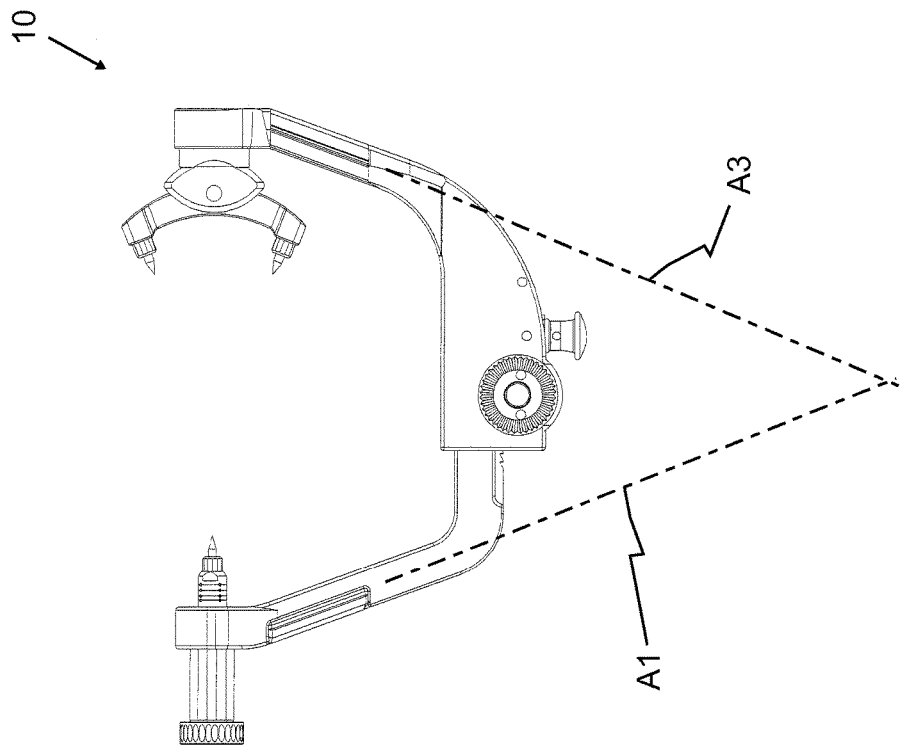
FIG. 3 depicts an alternate front view of the skull clamp of FIG. 1.
Figure 4:
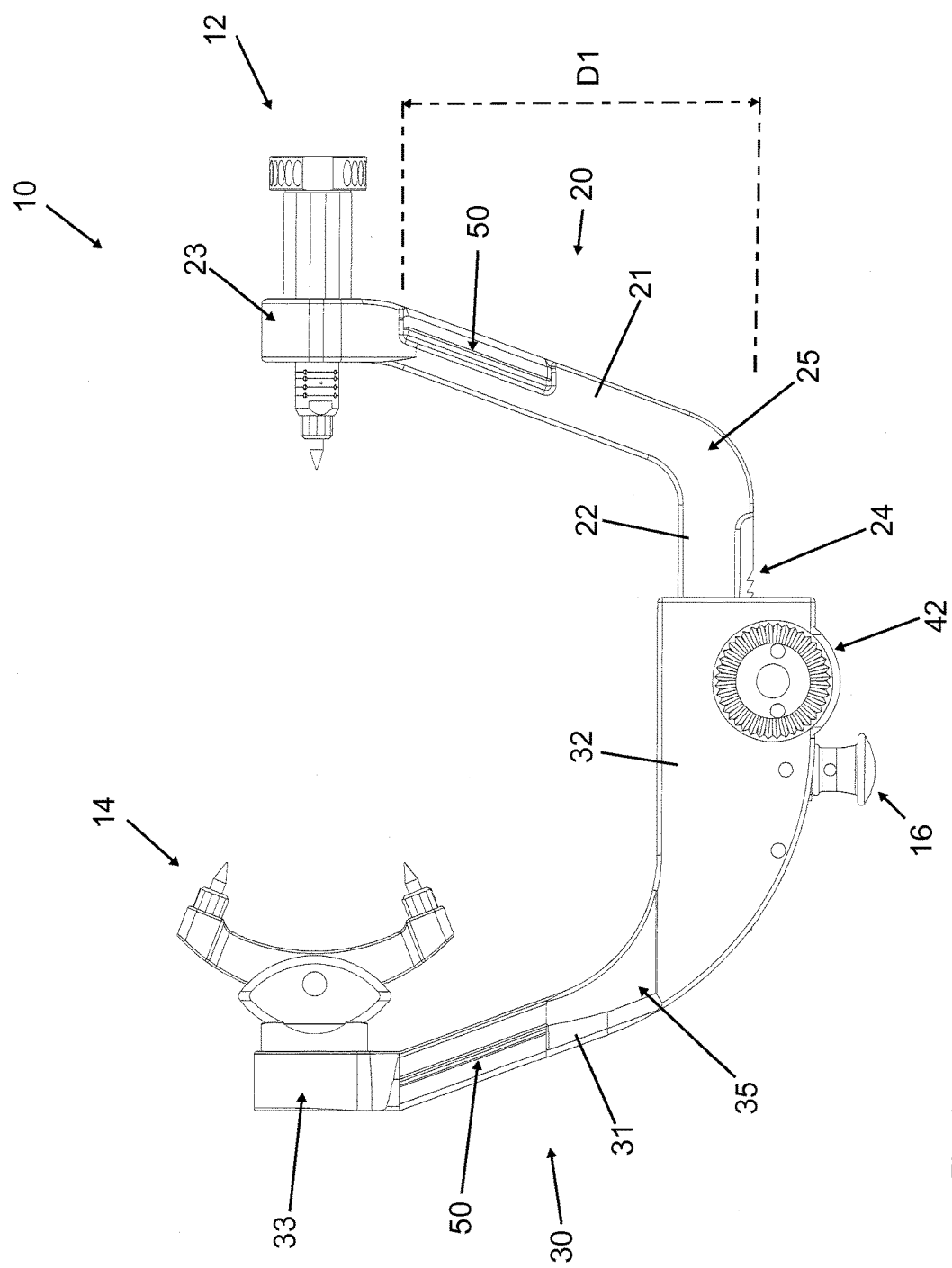
FIG. 4 depicts a back view of the skull clamp of FIG. 1.
Figure 5:
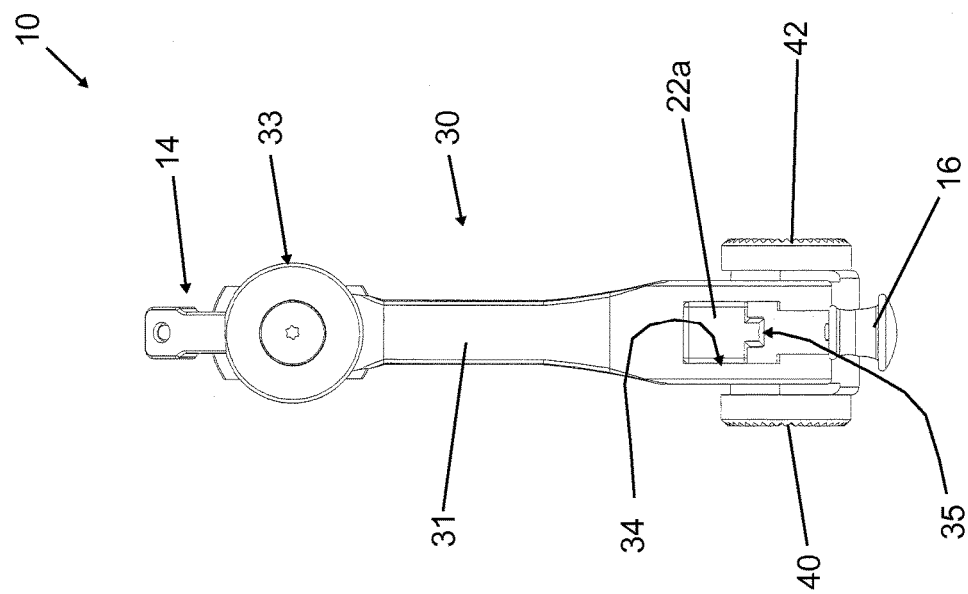
FIG. 5 depicts a side view of the skull clamp of FIG. 1.
Figure 6:
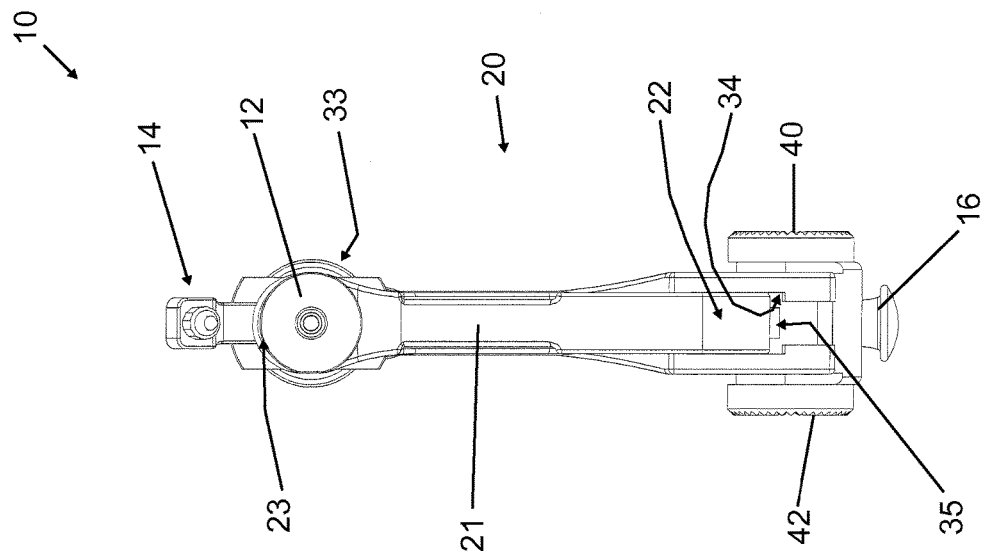
FIG. 6 depicts another side view of the skull clamp of FIG. 1, opposite the side view of FIG. 5.
Figure 7:
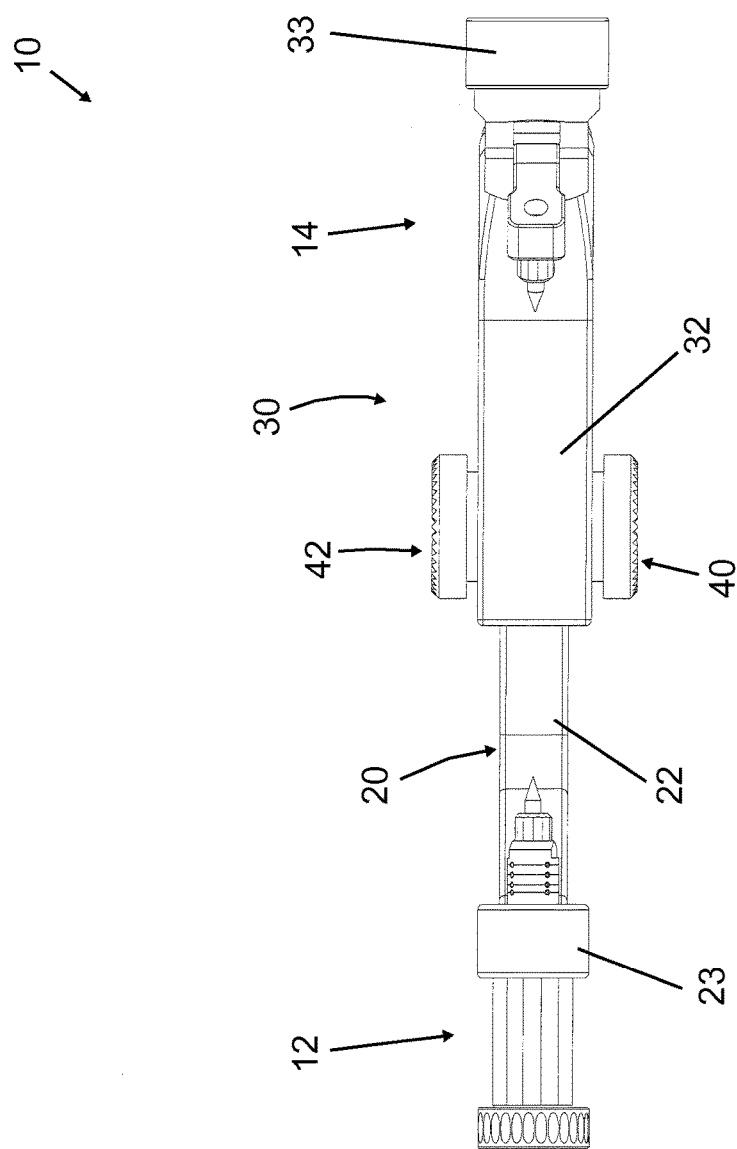
FIG. 7 depicts a top view of the skull clamp of FIG. 1.
Figure 8:
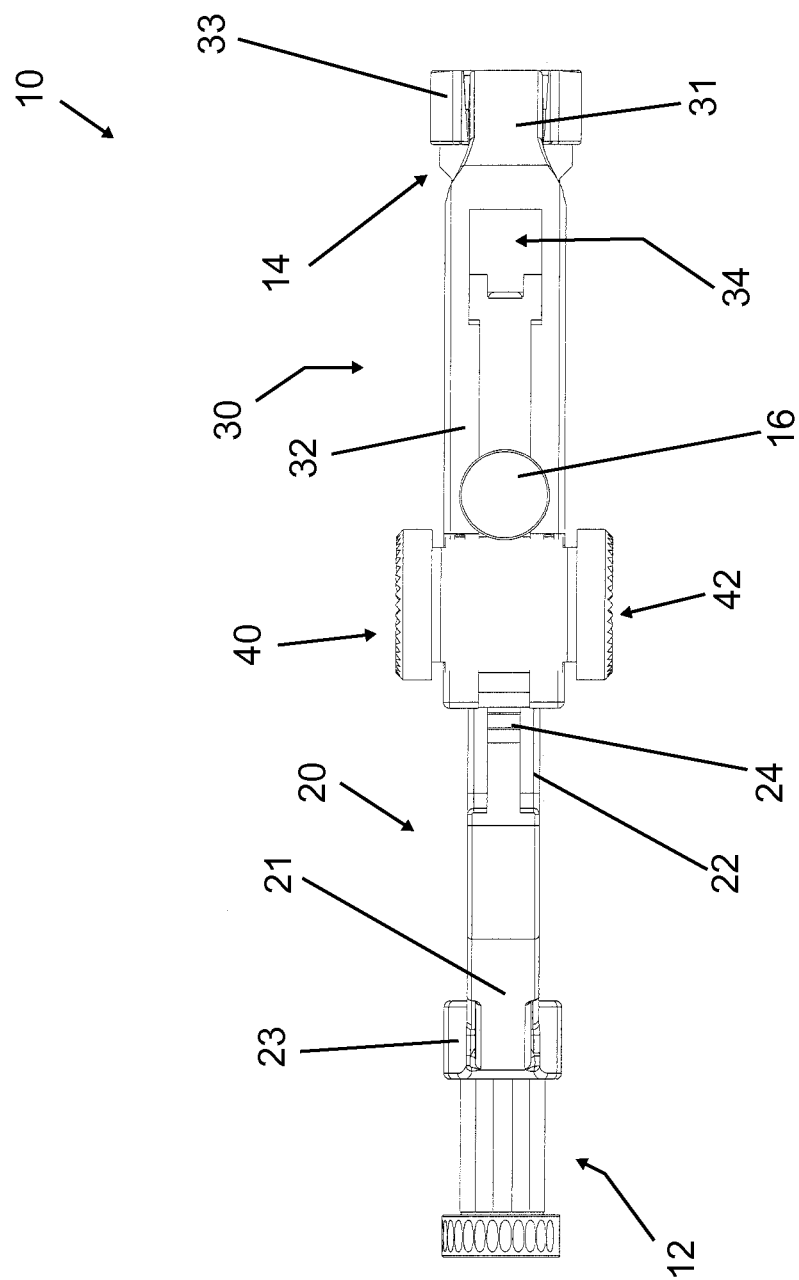
FIG. 8 depicts a bottom view of the skull clamp of FIG. 1.
Figure 9:
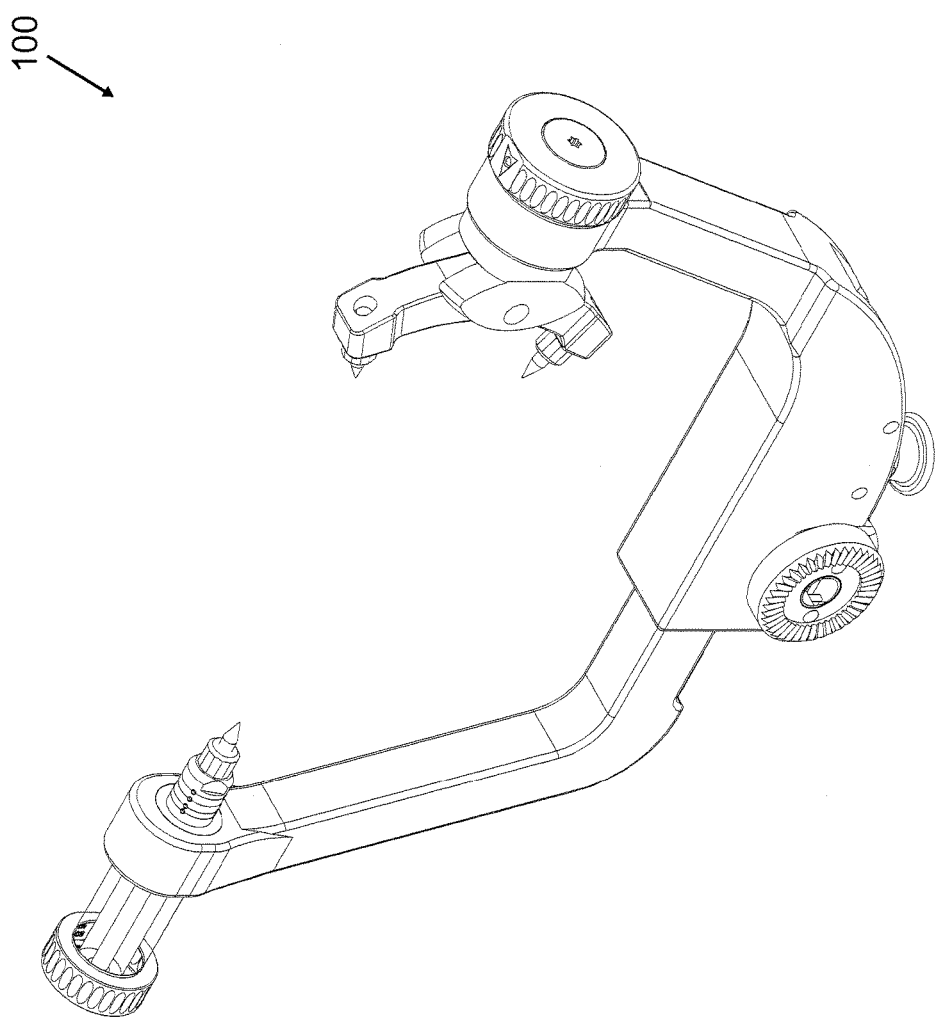
FIG. 9 depicts a perspective view of another example skull clamp, shown without a rail portion.

This is best shown in the front and back views of FIGS. 2-4. For instance, FIG. 2 depicts axes A1 and A2 that intersect and represent longitudinal axes defined by upright portion (21) and lateral portion (22). The angle (B1) formed by intersecting axes A1 and A2 is not 90 degrees, but instead an obtuse angle greater than 90 degrees. Similarly with respect to arm (30), axes A3 and A4 are shown and intersect and represent longitudinal axes defined by upright portion (31) and lateral portion (32). The angle (B2) formed by intersecting axes A3 and A4 is not 90 degrees, but instead an obtuse angle greater than 90 degrees. More specifically, the angles (B1, B2) formed by intersecting longitudinal axes defined by upright portions (21, 31) and respective lateral portions (22, 32) are between about 100 degrees and 120 degrees. In some examples the angles (B1, B2) are about 110 degrees.

From the above description, upright portions (21, 31) and their respective lateral portions (22, 32) can also be described as forming a V-shape where the angle about the vertex of the V-shape (which would coincide with angles (B1, B2)) is obtuse or greater than about 90 degrees. Furthermore, this configuration is present in the arrangement of both arms (20, 30) of skull clamp (10) such that this configuration exists on both sides of skull clamp (10). In other words, skull clamp (10) comprises arm (20) and arm (30) where each of arms (20, 30) comprise a V-shape forming an obtuse angle.

Figure 10:
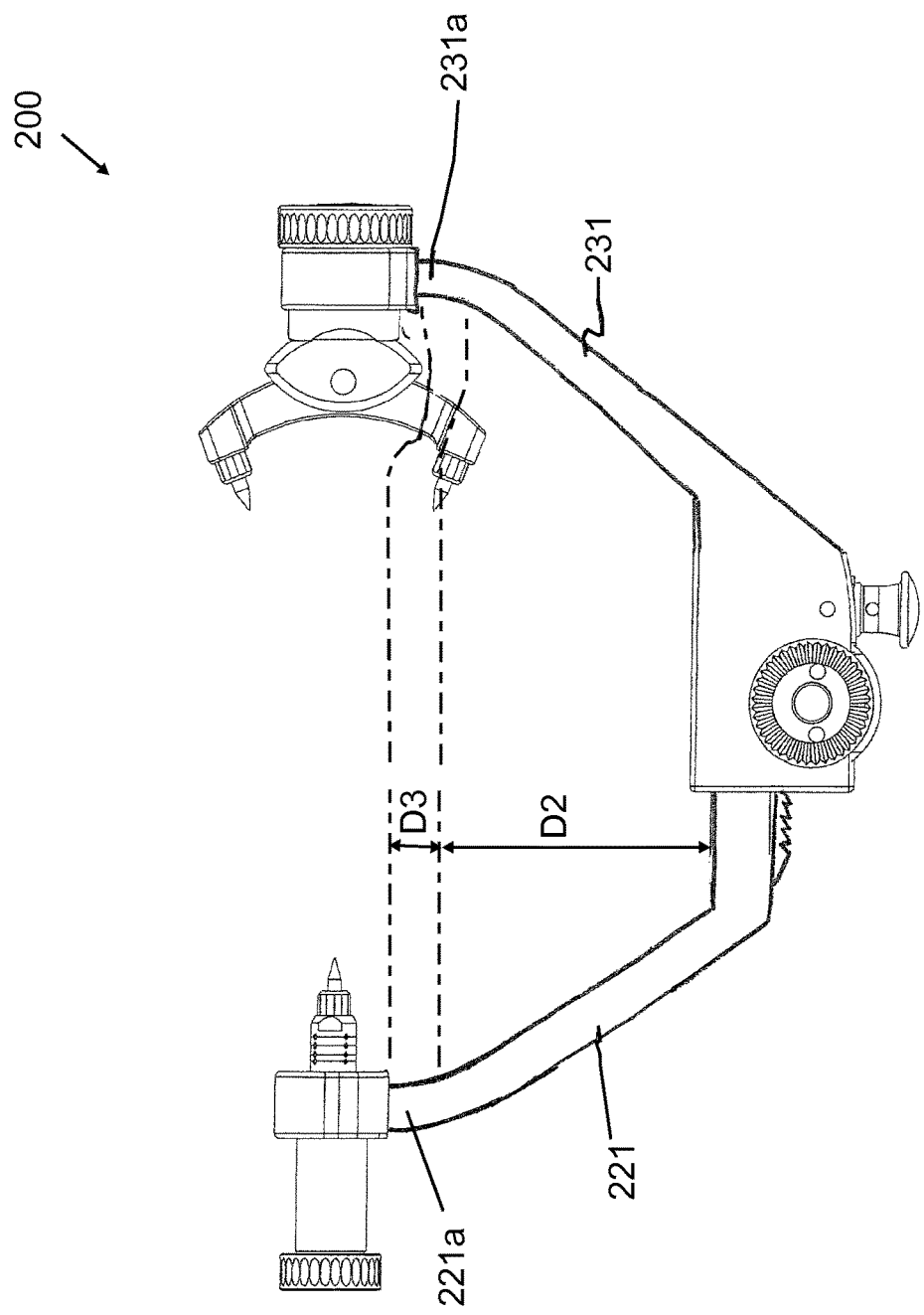
FIG. 10 depicts another example skull clamp.

In the present examples, the V-shape of arm (20) is defined by lateral portion (22) and the part of upright portion (21) extending all the way to first end (21a) that connects with end (23), which is configured to receive pin holding assembly (12). Similarly, arm (30) is defined by lateral portion (32) and the part of upright portion (31) extending all the way to first end (31a) that connects with end (33), which is configured to receive pin holding assembly (14). In some other examples, the V-shape may be defined by lateral portions (22, 32) and part of the respective upright portions (21, 31) that extends most of the way toward respective first ends (21a, 31a) but not required to extend all the way to respective first ends (21a, 31a). In other words, the V-shape may be defined by lateral portions (22, 32) and about e.g. 70% of the length of respective upright portions (21, 31) beginning from respective second ends (21b, 31b). By way of example only, FIG. 10 depicts another skull clamp (200) that shows where the V-shape of the arms is defined by lateral portions and respective parts of upright portions not extending all the way to the first ends of upright portions, but extending most of the way toward first ends.

As mentioned above, upright portions (21, 31) of skull clamp (10) define longitudinal axes (A1, A3). More specifically, longitudinal axes (A1, A3) are defined by the regions of upright portions (21, 31) that extend all the way to respective first ends (21a, 31a). In other words, longitudinal axes (A1, A3) of upright portions (21, 31) extend to and/or through respective first ends (21a, 31a). Stated another way, the regions or parts of upright portions (21, 31) that connect with ends (23, 33) that receive respective pin holding assemblies (12, 14) define longitudinal axes (A1, A3) of upright portions (21, 31) that ultimately intersect with longitudinal axes (A2, A4) of lateral portions (22, 32) to define the obtuse angles mentioned above (B1, B2).

Skull clamp (10) can also be considered to form a V-shape based on the intersection of longitudinal axes (A1, A3) of upright portions irrespective of their intersection with longitudinal axes (A2, A4). In this configuration, when longitudinal axes (A1, A3) are extended they converge beneath lateral portions (22, 32) of skull clamp (10), until they ultimately intersect as shown in FIG. 3. In this fashion, longitudinal axes (A1, A3) that extend to and/or through first ends (21a, 31a) of respective upright portions (21, 31) define a V-shape where the vertex, or intersection point of longitudinal axes (A1, A3), is beneath lateral portions (22, 32) of skull clamp (10).

Skull clamp (10) comprises lateral portions (22, 32) and upright portions (21, 31) as described above. The distance between upright portions (21, 31) can represent a width dimension, or X-direction, of skull clamp (10). The vertical distance along upright portions (21, 31) can represent a height dimension, or Y-direction, of skull clamp (10). X and Y axes are shown if FIG. 2 to depict these directions. With skull clamp (10), excluding pin assemblies (12, 14), the largest width of skull clamp (10) occurs at first ends (21a, 31a) of upright portions (21, 31). This can also be stated that the largest width of skull clamp (10) occurs at ends (23, 33) since ends (23, 33) connect with first ends (21a, 31a) and extend upward from there. So the widest point of skull clamp (10) can be regarded as at or just below where pin assemblies (12, 14) are received within skull clamp (10). Skull clamp (10) further has a changing width along the height of skull clamp (10). For instance, the distance between upright portions (21, 31) increases when moving along upright portions (21, 31). In the present example, but not necessarily required in all versions, this increasing distance between upright portions (21, 31) begins from near lateral portions (22, 32) extending upward toward ends (23, 33).

In the exemplary clamp (10) shown in FIGS. 1-8, arms (20, 30) of skull clamp (10) maintain an outward angle from the base of skull clamp (10)—e.g. where lateral portions (22, 32) reside—all the way to first ends (21a, 31a) of upright portions (21, 31) where they join with respective ends (23, 33) for receiving pin assemblies (12, 14). Maintaining this outward angle of both arms (20, 30) provides for the increasing width along the height of skull clamp (10) as mentioned above. In some other examples, skull clamps can maintain an outward angle from the base of skull clamp along a substantial length of upright portions, but is not required to maintain an outward angle all the way to the first ends of the upright portions. By way of example, in some instances the outward angle exists from the second end (22b) of lateral portion (22) and continues for at least 30% of the vertical distance (D1) or height towards the end of upright portions (21, 31) where upright portion (21, 31) connects with ends (23, 33). FIG. 4 includes an annotation depicting this vertical distance (D1) mentioned here. In other versions, this percentage is greater, for instance between or equal to 30% and 90%. Still in some versions this percentage is about 50% or greater, while in other versions the percentage is about 70% or greater.

In another example as shown in FIG. 10, skull clamp (200) maintains an outward angle from the base of skull clamp (200) along a substantial length of upright portions (221, 231) but not all the way to first ends (221a, 231a) of upright portions (221, 231). Accordingly, the width of skull clamp (200) increases from the base of skull clamp (200) (in the region of D2 as shown in FIG. 10) and then transitions to remain generally constant to first ends (221a, 231a) (in the region of D3 as shown in FIG. 10). In another example as shown in FIG. 11, skull clamp (300) includes upright portions (321, 331) that are curved such that skull clamp (300) forms, not an outward angle formed from the intersection of longitudinal axes of upright portions and lateral portions, but instead a radius of curvature of upright portions (321, 331) that begins at the connection of upright portions (321, 331) with lateral portions (322, 332) and extends to first ends (321a, 331 a).

As described herein, the term "outward angle," "outwardly angled," and similar terms, can be understood to mean that upright portions (21, 31) extend from lateral portions (22, 32) in a direction away from a midline or centerline (C1) of skull clamp (10) as shown in FIG. 2. Moreover, when both arms (20, 30) have an outward angle the distance or width between upright portions (21, 31) will increase as upright portions (21, 31) extend toward ends (23, 33) as described above.

In the illustrated example, arms (20, 30) of skull clamp (10) are each angled to generally the same degree or amount such that arm (20) is oriented in a similar angled fashion to arm (30) and vice versa. In some other examples, this is not required and arm (20) may have a greater or lesser angle (B1) compared to the angle (B2) for arm (30). The term or phrase "arm angle" or "angle of the arm" or similar terms or phrases as used herein can be understood to mean the angle created by the intersection of longitudinal axes defined by upright portions (21, 31) with respective lateral portions (22, 32) of arms (20, 30). In view of the teachings herein, other angles and configurations for skull clamp (10) and arms (20, 30) will be apparent to those of ordinary skill in the art.

As shown and described above, the angular configuration of arms (20, 30) of skull clamp (10) provide a fixture for stabilizing a portion of a patient, where skull clamp (10) can have a smaller footprint than other conventional similar fixtures, especially around regions of skull clamp (10) below the pin holder assemblies (12, 14) and near the base of skull clamp (10). The smaller footprint is largely due to the arrangement of the upright portions (21, 31) relative to the lateral portions (22, 32) of arms (20, 30). By using an angular arrangement where the arm angle is not perpendicular, but instead an angle greater than 90 degrees, skull clamp (10) takes up less space. This space-saving configuration makes skull clamp (10) better suited for use in tight spaces like where imaging techniques are used while a patient is immobilized using skull clamp (10). More specifically, the smaller footprint and shape characteristics of clamps (10, 100, 200, 300) described above help prevent collision with scanners or tables in certain intra-operative imaging procedures where skull clamps are used.

In some versions, a skull clamp as described herein can be used in a medical procedure to stabilize a patient with the skull clamp having and opening with a width near the base of the skull clamp that is about 50% to 70% of the opening's width at or near the top of the skull clamp. In a more specific example, a skull clamp includes a first arm comprising a first straight upright portion associated with a first end configured to hold a first pin assembly, the first arm further comprising a first straight lateral portion. The skull clamp further includes a second arm having a second straight upright portion associated with a second end configured to hold a second pin assembly, the second arm further comprising a second straight lateral portion. The distance between the first straight upright portion and the second straight upright portion define an opening of the skull clamp for receiving a patient's head. The opening comprises a first width at about where the first and second straight upright portions connect with the respective first and second straight lateral portions. The opening further comprises a second width at about where the first and second straight upright portions connect with the respective first and second ends configured to hold the respective first and second pin assemblies. The first width is about 50% to 70% of the distance of the second width. In some versions the first width is about 55% to 65% of the distance of the second width. Still in some versions the first width is about 60% of the distance of the second width.

Arms (20, 30) of skull clamp (10) also comprise curved portions (25, 35) respectively in the illustrated version. In some other examples curved portions (25, 35) may be omitted. In some other examples curved portions (25, 35) may be extended. In the present example, curved portions (25, 35) are configured to provide a gradual transition along respective arms (20, 30) between upright portions (21, 31) and lateral portions (22, 32).

Arms (20, 30) of skull clamp (10) also comprise a generally cuboid shape. With such a shape, the cross-sections along upright portions (21, 31) and lateral portions (22, 32), taken perpendicular to the longitudinal axes defined by the upright portions (21, 31) and lateral portions (22, 32), generally have a rectangular shape. In other examples, arms (20, 30) may have a cylindrical shape where the cross-sections described above would have a circular shape. In view of the teachings herein, other shapes for arms (20, 30) of skull clamp (10) will be apparent to those of ordinary skill in the art.

Skull clamp (10) can be constructed from radiolucent materials in some examples. For instance skull clamp (10) may be constructed from PEEK or other suitable polymeric materials. In other examples, skull clamp (10) can be constructed of non-magnetic metals, such as aluminum or titanium. In applications where skull clamp (10) will be used with certain imagining techniques and equipment, skull clamp (10) can be constructed from either a material that is radiolucent such that skull clamp (10) does not appear on the imaging output, or skull clamp (10) can be constructed from a material that is not radiolucent yet is compatible with known imagining modalities. In view of the teachings herein, various construction materials for skull clamp (10) will be apparent to those of ordinary skill in the art.

It should be understood that any one or more of the teachings, expressions, embodiments, examples, etc. disclosed herein may be combined with any one or more of the other teachings, expressions, embodiments, examples, etc. that are disclosed herein. The teachings, expressions, embodiments, examples, etc. disclosed herein should therefore not be viewed in isolation relative to each other. Various suitable ways in which numerous aspects of the present disclosure may be combined will be readily apparent to those of ordinary skill in the art in view of the teachings disclosed herein. Such modifications and variations are intended to be included within the scope of both the present disclosure and the claims.

Having shown and described various embodiments of the present disclosure, further adaptations of the methods and systems described herein may be accomplished by appropriate modifications by one of ordinary skill in the art without departing from the scope of the present disclosure. Several of such potential modifications have been mentioned, and others will be apparent to those skilled in the art. For instance, examples, embodiments, geometrics, materials, dimensions, ratios, steps, and the like discussed above are illustrative and are not required. Accordingly, the scope of the present disclosure should be considered in terms of the following claims and is understood not to be limited to the details of structure and operation shown and described in the specification and drawings.

I claim:

1. A skull clamp for use in a medical procedure to stabilize a patient, comprising:
   a. a first arm, wherein the first arm comprises a first upright portion having a first end and a second end, wherein the first arm further comprises a first bore configured to receive a first pin assembly, wherein the first bore is connected with the first upright portion at the first end, and wherein the first arm further comprises a first lateral portion, wherein the first lateral portion is connected with the first upright portion at the second end, wherein the first upright portion defines a first longitudinal axis extending through the first end and the second end, wherein a substantial length of the first upright portion from the first end to the second end is parallel to the first longitudinal axis;
   b. a second arm, wherein the second arm comprises a second upright portion having a first end and a second end, wherein the second arm further comprises a second bore configured to receive a second pin assembly, wherein the second bore is connected with the second upright portion at the first end, and wherein the second arm further comprises a second lateral portion, wherein the second lateral portion is connected with the second upright portion at the second end, wherein the second upright portion defines a second longitudinal axis extending through the first end and the second end, wherein a substantial length of the second upright portion from the first end to the second end is parallel to the second longitudinal axis;
   c. wherein adjustment of the first and second arms of the skull clamp is limited to adjusting the spacing between the first and second arms while the length of the first and second upright portions is non-adjustable; and
   d. wherein the first and second longitudinal axes intersect below a base defined by the first and second lateral portions of the skull clamp and form a V-shape.

2. The skull clamp of claim 1, wherein the first lateral portion of the first arm defines a third longitudinal axis, wherein the second lateral portion of the second arm defines a fourth longitudinal axis.

3. The skull clamp of claim 2, wherein the first longitudinal axis and the third longitudinal axis intersect to form an obtuse angle.

4. The skull clamp of claim 3, wherein the second longitudinal axis and the fourth longitudinal axis intersect to from an obtuse angle.

5. The skull clamp of claim 1, further comprising an integrated rail portion on a select one or more of the first upright portion and the second upright portion of the respective first and second arms.

6. The skull clamp of claim 5, wherein the integrated rail portion is limited to being parallel with the select one or more of the first upright portion and the second upright portion.

7. The skull clamp of claim 1, wherein a width of the skull clamp increases such that the width of the skull clamp at the second end of the first upright portion and the second end of the second upright portion is about 50 to 70 percent of the width of the skull clamp at the first bore connected with the first end of the first upright portion and the second bore connected with the first end of the second upright portion.

* * * * *